(12) United States Patent
Evans et al.

(10) Patent No.: US 6,520,933 B1
(45) Date of Patent: Feb. 18, 2003

(54) CENTRAL VENOUS LINE COOLING CATHETER HAVING A SPIRAL-SHAPED HEAT EXCHANGE MEMBER

(75) Inventors: Scott Evans, Santa Ana, CA (US); Blair Walker, Mission Viejo, CA (US); Wayne Noda, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 43 days.

(21) Appl. No.: 09/704,778

(22) Filed: Nov. 3, 2000

Related U.S. Application Data

(63) Continuation-in-part of application No. 09/503,014, filed on Feb. 11, 2000, now Pat. No. 6,409,747, and a continuation-in-part of application No. 09/253,109, filed on Feb. 19, 1999, now abandoned, which is a continuation of application No. 09/063,984, filed on Apr. 21, 1998, now Pat. No. 6,126,684.

(51) Int. Cl.[7] .................. A61M 31/00; A61M 37/00
(52) U.S. Cl. .................. 604/103.07; 604/103.08; 604/113; 604/101.05; 606/23; 606/21; 607/105
(58) Field of Search .................. 604/96.01, 174, 604/113, 101.05, 523, 103.07, 103.08; 606/21–26, 194; 607/96, 102, 104–107

(56) References Cited

U.S. PATENT DOCUMENTS

| | | |
|---|---|---|
| 4,546,759 A | 10/1985 | Solar |
| 4,897,082 A | 1/1990 | Erskine |
| 5,015,230 A | 5/1991 | Martin et al. |
| 5,271,743 A | 12/1993 | Hattler |
| 5,346,508 A | 9/1994 | Hastings |
| 5,383,856 A | 1/1995 | Bersin |
| 5,423,763 A | 6/1995 | Helland et al. |
| 5,478,309 A | 12/1995 | Sweezer et al. |
| 5,498,261 A | 3/1996 | Strul |
| 5,549,559 A | 8/1996 | Eshel |
| 5,624,392 A | 4/1997 | Saab |
| 5,716,386 A | 2/1998 | Ward et al. |
| 5,735,816 A | 4/1998 | Lieber et al. |
| 5,749,852 A | 5/1998 | Schwab et al. |
| 5,807,342 A | 9/1998 | Musgrave et al. |
| 5,879,316 A | 3/1999 | Safar et al. |
| 5,891,386 A | 4/1999 | Deitermann et al. |
| 5,902,274 A | 5/1999 | Yamamoto et al. |
| 5,906,588 A | 5/1999 | Safar et al. |
| 5,957,963 A | 9/1999 | Dobak, III |
| 6,051,019 A | 4/2000 | Dobak, III |
| 6,056,837 A | 5/2000 | Lieber et al. |
| 6,093,199 A | 7/2000 | Brown et al. |
| 6,096,068 A | 8/2000 | Dobak et al. |
| 6,126,684 A | 10/2000 | Gobin et al. |
| 6,190,356 B1 | 2/2001 | Bersin |
| 6,231,594 B1 | 5/2001 | Dae |
| 6,261,312 B1 * | 7/2001 | Dobak et al. .................. 606/21 |
| 6,287,326 B1 | 9/2001 | Pecor |

OTHER PUBLICATIONS

U.S. patent application Ser. No. 09/133,813, Noda et al., app pending.
U.S. patent application Ser. No. 09/253,109, Evans et al., app pending.
U.S. patent application Ser. No. 09/294,080, Walker et al., app pending.

(List continued on next page.)

*Primary Examiner*—Brian L. Casler
*Assistant Examiner*—Jeremy Thissell
(74) *Attorney, Agent, or Firm*—Finnegan, Henderson, Farabow, Garrett & Dunner, L.L.P.

(57) ABSTRACT

A catheter and a method of using the catheter are disclosed that serve to create an efficient and rapid controlled manner of regulating a patient's body temperature. The catheter is a heat exchange catheter insertable into a blood vessel of a patient, circulating a heat exchange fluid therein, and including a spiral-shaped inflatable balloon that mixes laminar layers of the heat exchange fluid flowing inside the balloon.

10 Claims, 9 Drawing Sheets

OTHER PUBLICATIONS

U.S. patent application Ser. No. 09/503,014, Gobin et al., app pending.
U.S. patent application Ser. No. 09/679,399, Noda et al., app pending.
U.S. patent application Ser. No. 09/671,114, Walker et al., app pending.
U.S. patent application Ser. No. 09/704,778, Evans et al., app pending.

* cited by examiner

CENTRAL VENOUS LINE COOLING CATHETER HAVING A SPIRAL-SHAPED HEAT EXCHANGE MEMBER

The present application is a continuation-in-part of application ser. No. 09/253,109, filed Feb. 19, 1999, now abandoned and is also a continuation-in-part of application Ser. No. 09/503,014, filed Feb. 11, 2000, now U.S. Pat. No. 6,409,747 which, in turn, is a continuation of application Ser. No. 09/063,984, filed Apr. 21, 1998, now U.S. Pat. No. 6,126,684, and claims the benefit thereof under 35 U.S.C. §120.

BACKGROUND OF THE INVENTION

1. Field of the Invention

The invention relates to catheters, and more particularly, to long-term indwelling catheters, used in the central venous system of a patient, for controlling patient body temperature.

2. Description of Related Art

Catheters such as central venous line catheters are typically used in ICU (intensive care unit) patients, particularly in those patients who have suffered a stroke or other brain traumatic event. The central venous line catheters are typically about 5.0–12 French in size and consist of a soft, flexible multi-lumen structure extending 6–12 inches. They are usually introduced through the subclavian or jugular vein, and less preferably in the femoral vein of the patient, serving to provide the caretaker with easy and convenient access to the patient's central blood supply via the central venous system. In this manner general access to the central blood supply is gained, enabling for example delivery of drugs, infusion fluids or nutrition, along with the gathering of patient blood for blood gas analysis, measurement of blood pressure, and the like.

In many patients, such as ICU patients, fever is a common occurrence. Fever is particularly likely in neuro-ICU patients, and its onset can exacerbate detrimental effects in the brain. Conventional therapies to control fever include treatment with acetaminophen (Tylenol), cooling blankets, ice water bladder lavages, and ice baths. All of these approaches to cooling a patient require excessive time to cool the patient. Moreover, prior methods do not provide for precise control of patient cooling. As recognized herein, to optimize the advantage of cooling a patient, it is important to cool the patient relatively quickly in a controlled fashion.

Indwelling catheters are known that can be implanted in the body of a patient to remove heat from the blood supply of the patient, thereby in turn reducing the patient's core body temperature. A known indwelling catheter is disposed in a heat exchange relationship with the blood supply, and a heat exchange fluid is circulated through a set of lumens and an inflatable balloon in a closed loop. The heat exchange fluid flowing in the balloon exchanges heat with blood flowing past the balloon, lowering the temperature of body tissue and, as mentioned above, thereby improving the patient's medical outcome.

The advantages of the above-referenced cooling catheter can be implemented into a central venous catheter configuration. As mentioned above, central venous catheters are commonly used in many ICU patients, including neuro-ICU patients, and it would be advantageous to provide a central venous catheter with the capability of cooling a patient effectively.

Heat transfer capacity of known cooling catheters is believed to be limited, because of two fluid dynamic actions. First, it appears that the cooling fluid flowing in the balloon separates into laminar layers, with a first layer flowing in a long path past the inner surface of the balloon, and one or more additional layers beneath the first layer, flowing in a shorter path along the axis of the catheter. The fluid in the lower additional layers does not flow adjacent to the blood, and does not exchange heat with the blood. Only the outer layer flowing past the inner surface of the balloon exchanges heat with blood outside the balloon, so not all of the cooling capacity of the fluid is utilized. Second, it appears that blood flowing in the vein also separates into laminar layers, with a first layer flowing past the outer balloon surface, and other layers above the first layer flowing past the vein's inner wall. Only the layer flowing past the balloon's outer surface is exposed to the cooling effect of the catheter, so not all of the blood is available to be cooled, again adversely affecting the catheter's heat exchange capacity.

SUMMARY OF THE INVENTION

The present invention obviates one or more shortcomings of the prior art by providing a central venous line catheter adapted to actively exchange heat with the body of the patient to thereby raise or lower the patient's body temperature as required. The central venous line is provided with a heat exchange element disposed in heat exchange relationship with the blood of the patient. The heat exchange element houses a circulating fluid therein, with the fluid being automatically cooled or warmed exteriorly of the patient's body in accordance with a patient temperature feedback scheme. The heat exchange element includes an inflatable balloon having a spiral configuration, which causes laminar layers of cooling fluid flowing in the balloon to mix together.

By supplementing the known functions of a central venous line catheter with the function of cooling or warming the patient's blood, the present invention takes advantage of existing access to the venous system and a single, relatively small incision, reducing the risk of additional complications. The access, typically through the subclavian, jugular or femoral veins, is to the central blood supply, via the central venous system, and is therefore particularly expedient, permitting efficient cooling or warming of patient body temperature. The term central venous system generally relates to the portion of the venous system which returns blood to the right side of the heart, including the inferior and superior vena cava. A particular advantage of the invention is that the cooling function is performed efficiently in tandem with a procedure which is known to be likely attended by fever, thus anticipating such fever and facilitating its control. The heat exchange relationship between the system and the central venous system of the patient can be maintained for a prolonged duration—for example, from about one hour to about twenty-nine days. Moreover, because cooling fluid flow layers in the spiral balloon are mixed, cooling capacity of the system is increased over that of known cooling balloon catheters.

The central venous line catheter in accordance with the invention comprises a tubular structure defining a plurality of lumens. At least two of these lumens convey heat exchange fluid to and from a heat exchange element disposed at a distal, implantable end of the central venous line catheter, while the rest of the lumens may be used to provide access to the central blood supply of the patient. The heat exchange element is in fluid communication with a temperature control module via a tubing set which conveys the heat exchange fluid between the components. The temperature control unit comprising a cooling and/or a heating device, operates in conjunction with a temperature controller to heat or cool the heat exchange fluid depending on a sensed temperature of the patient. The heat exchange element includes at least one expandable balloon having a spiral shape.

The system of the invention operates to maintain patient temperature at a desired level. Any deviation from the desired level automatically triggers corrective action, such as circulating cooled heat exchange fluid through the central venous line catheter to contend with the onset of fever. Additionally, the system is equipped with indicators which signal to the caretaker of the patient the sensed deviation, by for example sensing the increased workload of the system, in order to warn of adverse physiological changes besetting the patient, such as infection.

The invention thus provides a system controlling patient temperature using a central venous line catheter having a heat exchange element. The central venous line catheter is provided with one or more lumens, preferably for providing access to the central blood supply of the patient, and with additional lumens for communicating heat exchange fluid to the heat exchange element. Heat exchange fluid temperature is controlled through a feedback loop in which patient temperature is sensed and used to control a temperature control unit comprising a heating device and/or a cooling device in heat exchange relationship with the heat exchange fluid. A tubing set transports the heat exchange fluid between the central venous line and the temperature control unit, with a pump serving to circulate the fluid in a closed fluid circuit in the system. The heat exchange element has a spiral shape to promote mixing of the heat exchange fluid flowing in the element.

DESCRIPTION OF THE DRAWING(S)

Advantages of the present invention will be apparent to those skilled in the art through reading this specification in conjunction with the attached drawings, wherein like reference numerals are applied to like elements and wherein.

DESCRIPTION OF THE PREFERRED EMBODIMENTS

Figure 1:
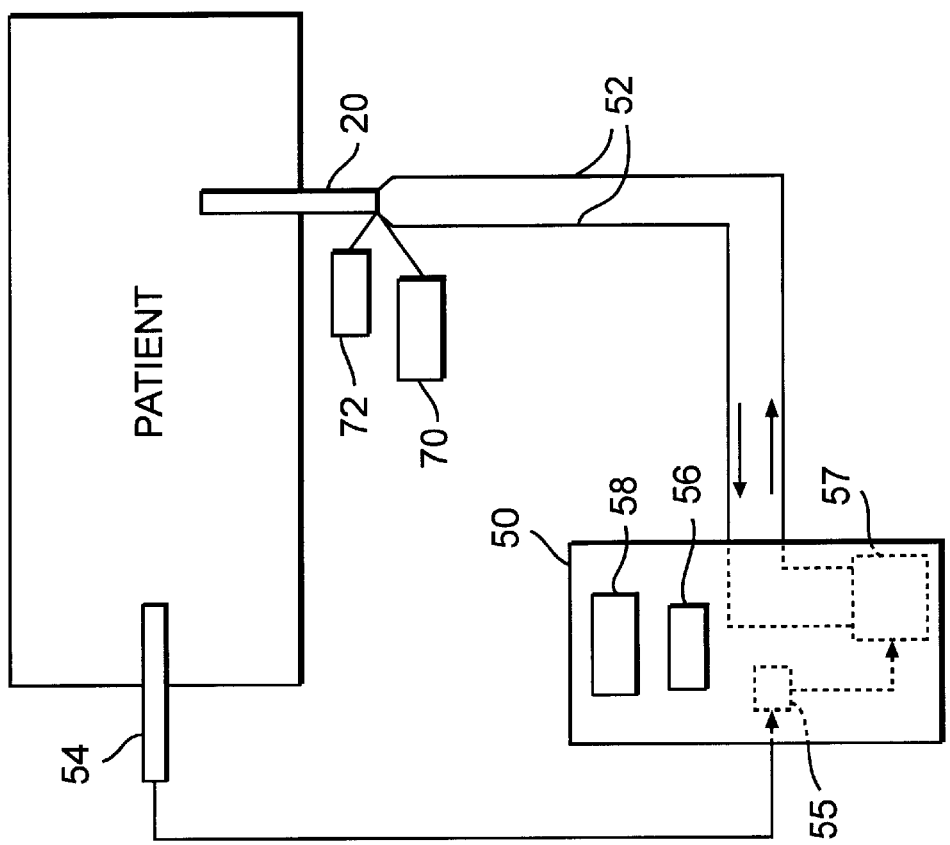
FIG. 1 is a schematic diagram showing a central venous line catheter temperature control system in accordance with the present invention.

FIG. 1 shows a temperature control system 10 in accordance with the invention. A central venous line catheter 20 providing access to the central blood supply of the patient is disposed in heat exchange relationship with the patient. Central venous line catheter 20 is provided with a circulating heat exchange fluid (not shown), the temperature of which is automatically controlled in accordance with a feedback scheme in order to achieve a desired patient target temperature or temperature range. The feedback schemes involves sensing patient temperature using a probe 54 whose output is provided to a temperature controller 55 housed in a temperature control module 50. The temperature controller 55 determines whether the sensed temperature represents a deviation from the desired temperature or range and selectively activates a heat control unit 57 in order to heat or cool the heat exchange fluid depending on the direction of deviation. As described in more detail below, the central venous line catheter 20 is a multi-lumen device, with at least two of the lumens being dedicated to heat exchange fluid flow to and from a heat exchange element of the catheter. The other lumen(s) can have different uses, if desired, such as fluid infusion or drug delivery, or guidewire support, depending on the particular application. The preferred number of lumens is 3 to 5, although other numbers of lumens are contemplated.

Figures 2, 8:
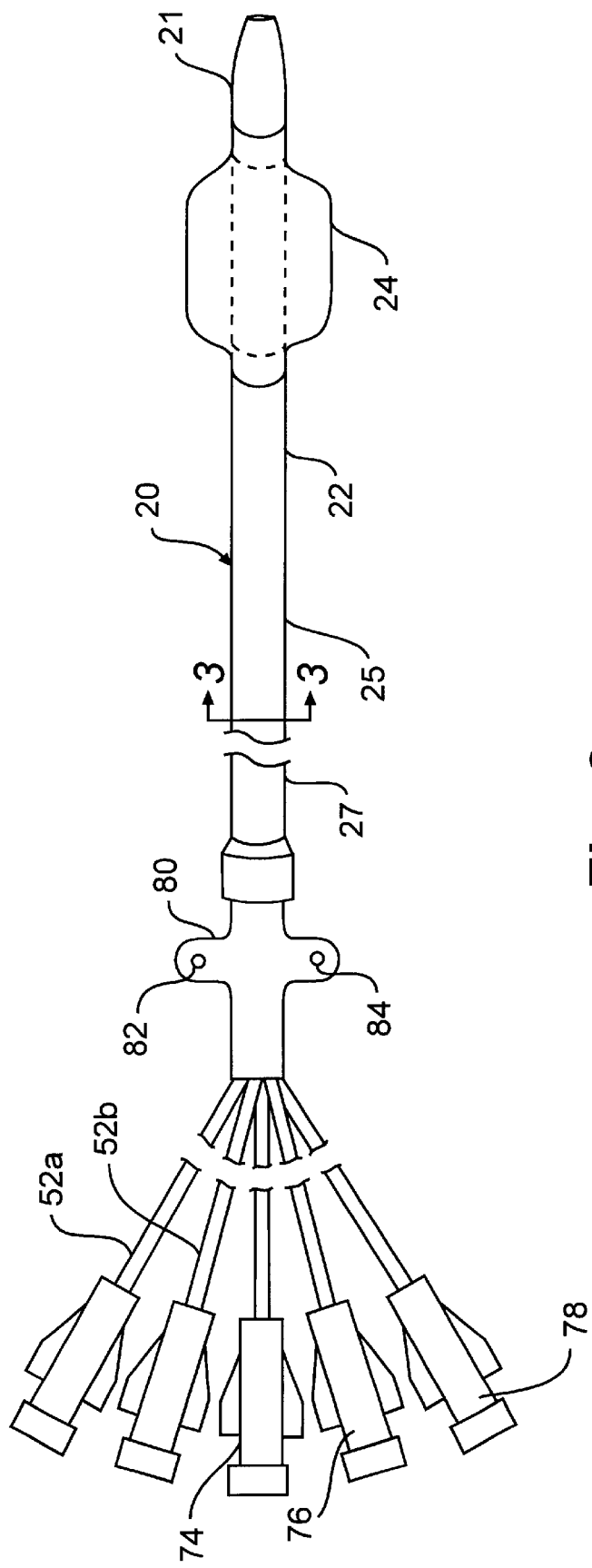
FIG. 2 is a schematic side elevational view of a central venous line catheter in accordance with the invention.
FIG. 8 is a perspective view of one embodiment of the present anchor.
Figure 4:
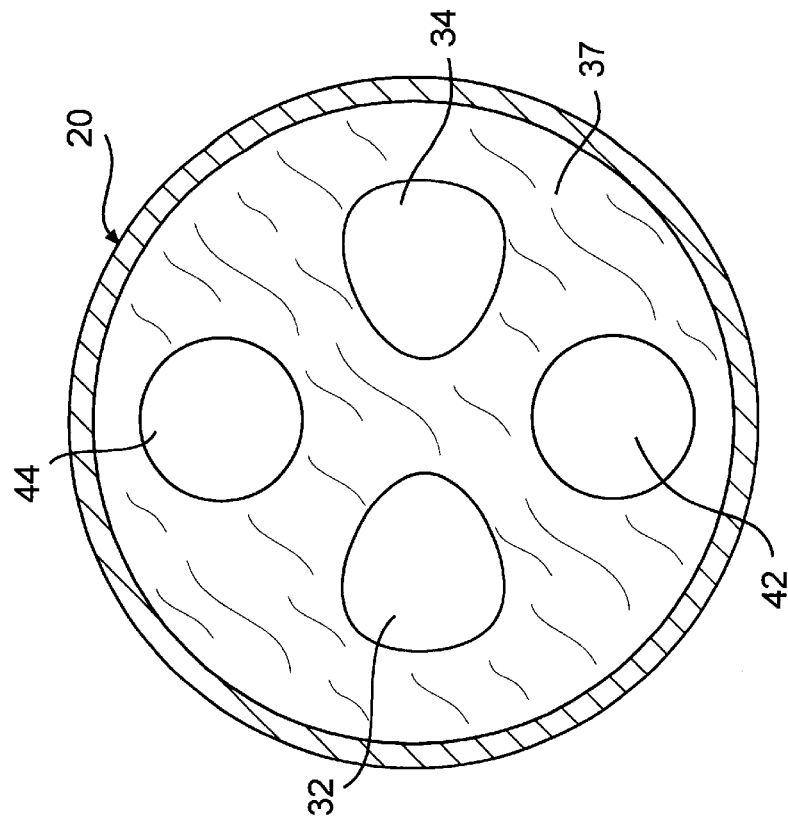
FIG. 4 is a schematic cross-sectional view of a preferred arrangement of a catheter in accordance with the invention.
Figure 3:
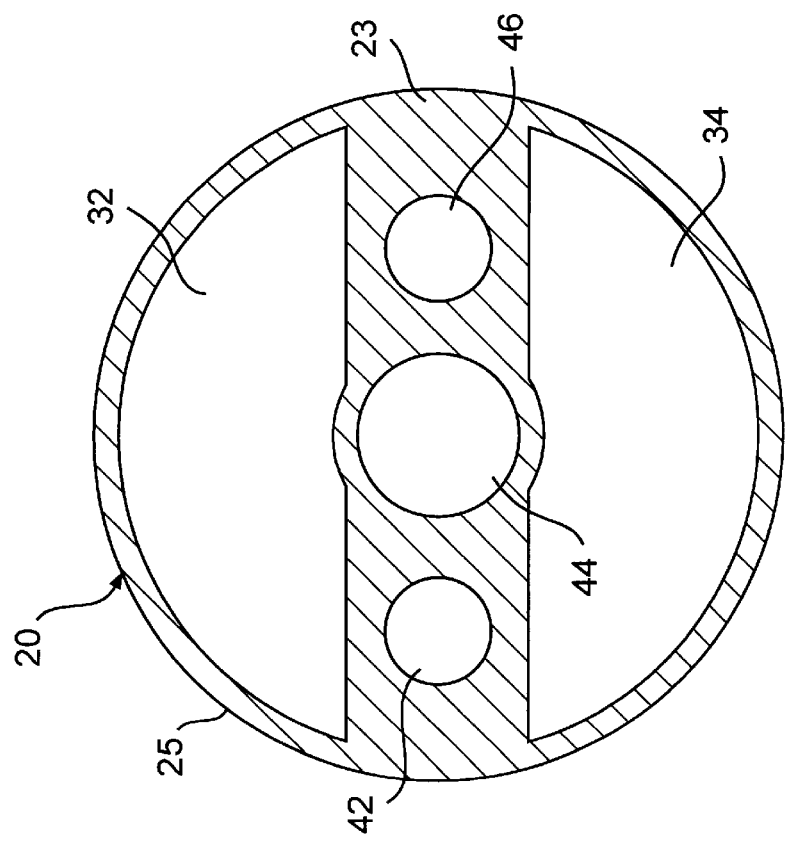
FIG. 3 is a schematic cross-sectional view taken along line 3—3 of FIG. 2.
Figure 5:
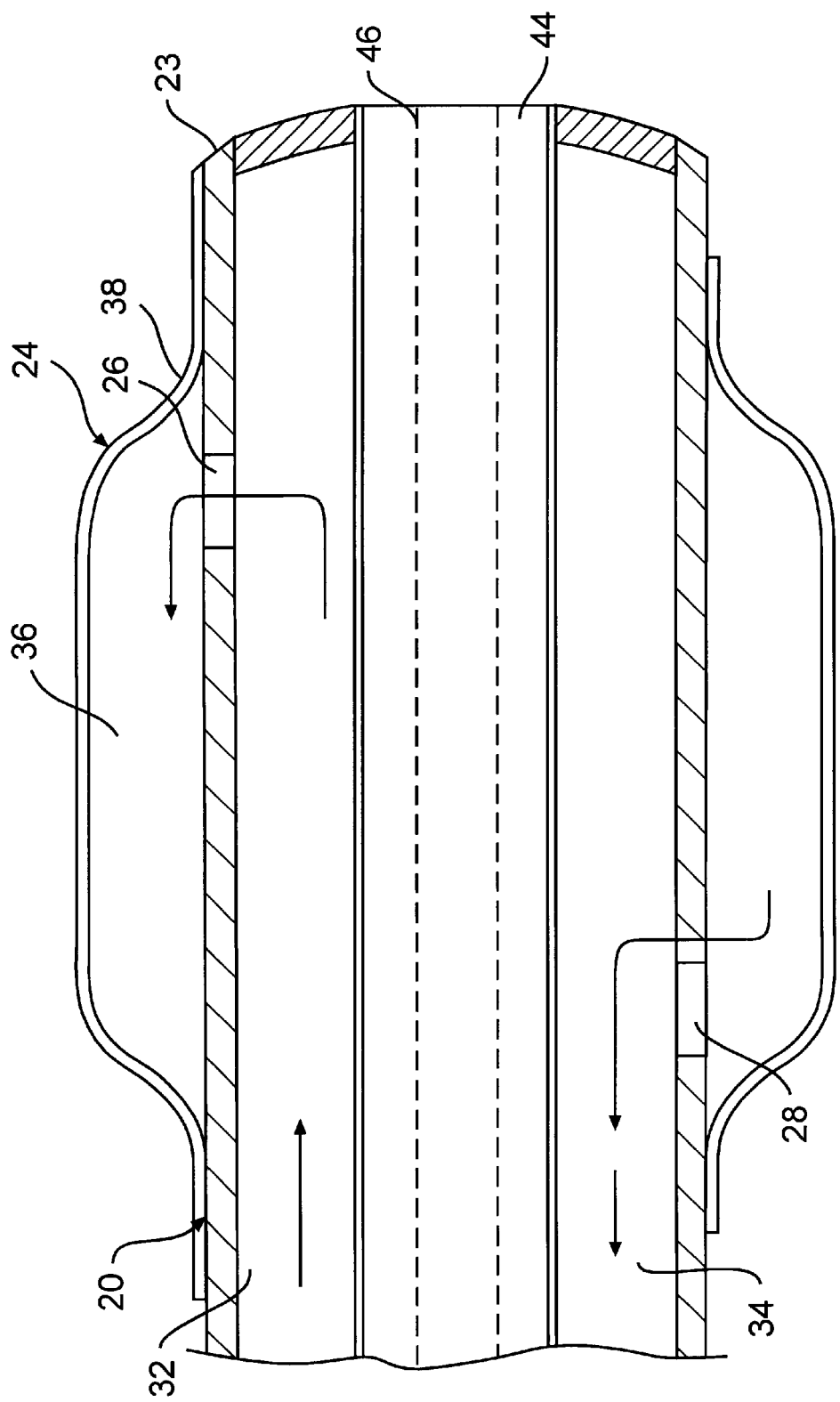
FIG. 5 is a schematic sectional view of the distal portion of the central venous line catheter of the invention.
Figure 6:
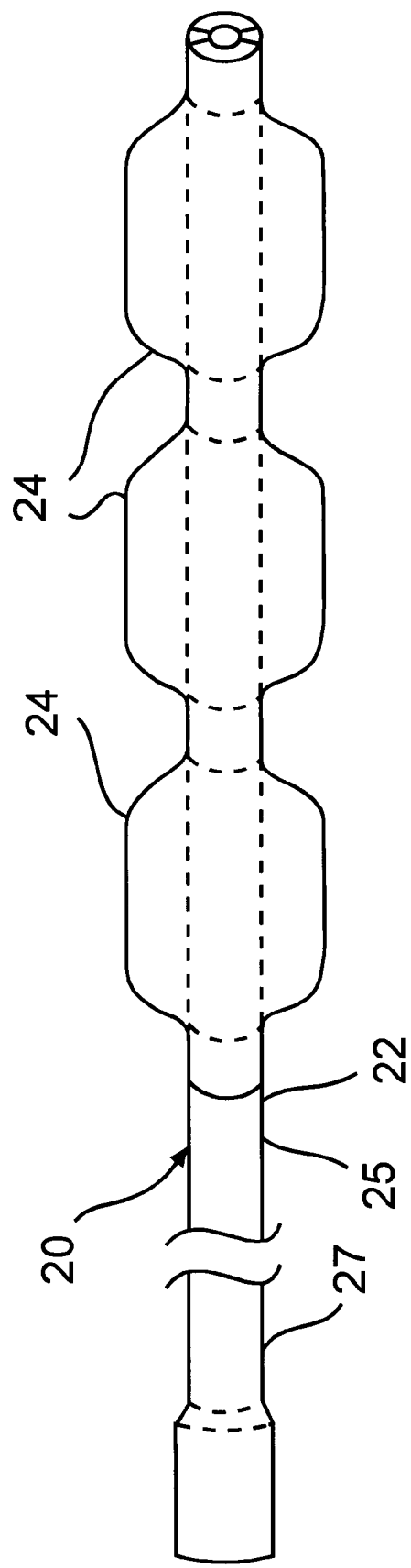
FIG. 6 is a schematic side elevational view of a central venous line catheter in accordance with a second embodiment of the invention.

FIGS. 2–4 show in more detail the central venous line catheter 20, which is a substantially elongate structure of generally cylindrical shape adapted for insertion into a body of a patient, preferably into the subclavian or jugular veins. Central venous line catheter 20 is formed of any known polymer material defining a shaft 25, housing various lumens 32, 34, 42, 44 and 46. A preferred material for shaft 25 is polyurethane, although other materials, such as nylon, polyethylene and PEBAX, can also be used. Considerations in selecting the appropriate material include biocompatability, flexibility, temperature change compatibility, and resistance to buckling. Shaft 25 has an outer diameter OD.

At its distal, implantable end portion 22, catheter 20 is provided with a heat exchange element such as a fluid-carrying inflatable balloon 24 that is radially disposed around the width of the catheter. Balloon 24 is disposed in the vicinity of flexible tip 21 and can be formed from a piece of flexible sheet material 38 formed into a molded balloon of the desired shape and size and then bound or otherwise fixed to the shaft 25 to form a cavity 36. Preferably, the balloon can be molded from a tube. As illustrated, balloon 24, when inflated, is shown to have a slightly larger outer diameter than the OD of shaft portion 25 of the catheter. Preferably, the outer diameter of the balloon is selected to be no more than 40%–60% of the diameter of a typical vena cava. It is to be appreciated that in some cases it may be desirable to maximize the diameter OD of the shaft 25 in order to facilitate heat exchange fluid flow. This will also minimize the volume of fluid in the balloon 24 and promote a more rapid heat exchange. In one preferred embodiment, the balloon 24 is made of flexible urethane, nylon, or PET and is thin-walled, i.e., the balloon 24 has a wall thickness of less than three mils, and more preferably less than one and one-half mils. Also, the balloon 24 preferably is coated with an antimicrobial substance, as well as an anticlot substance, such as heparin. The expandability of the balloon provides additional advantages. The balloon, when collapsed, has numerous wrinkles and folds in its surface. When the balloon 24 is substantially fully expanded, however, its outer surface is substantially smooth and wrinkle-free. This substantially wrinkle-free surface enables the heat exchange fluid inside the balloon to flow smoothly and efficiently past the inner surface, avoiding eddies and turbulence, which could be caused by folds or wrinkles in the material, which could increase pressure and fluid resistance. Likewise, blood flowing in the blood vessel outside the balloon 24 can flow smoothly and efficiently past the balloon's outer surface, without eddies or turbulence which could be caused by folds or wrinkles, which could create stagnation and possibly contribute to clotting.

Figure 9:
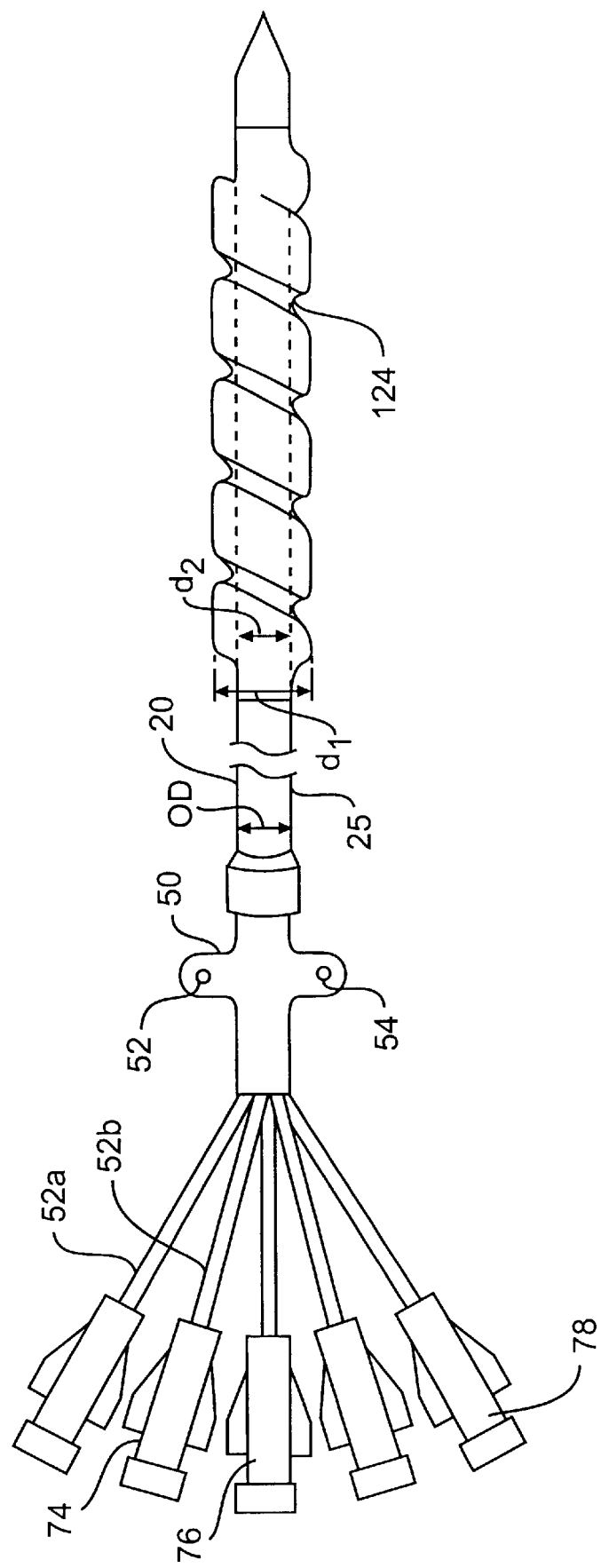
FIG. 9 is a schematic side elevational view of a central venous line catheter having a spiral balloon in accordance with the invention.
Figure 10:
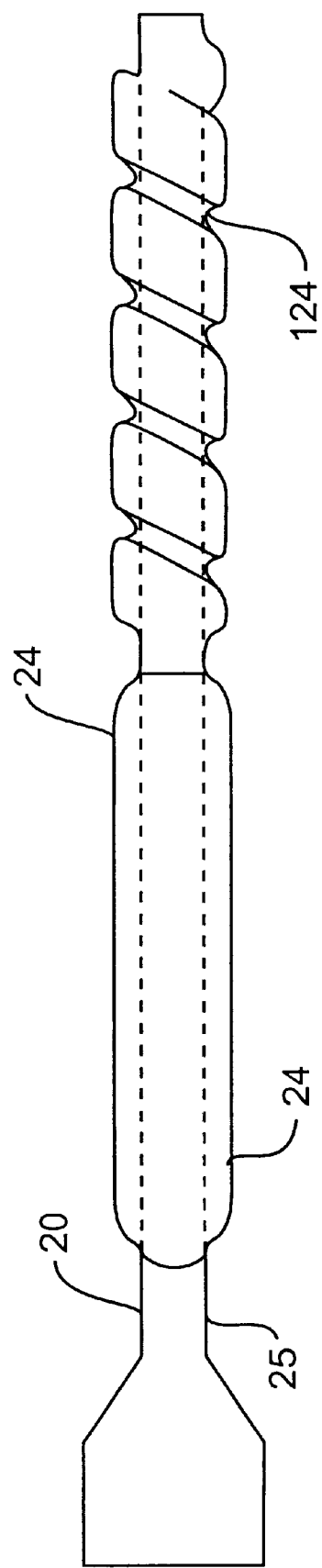
FIG. 10 is a schematic side elevational view of a portion of a central venous line catheter having both a spiral balloon and a straight balloon.
Figure 11:
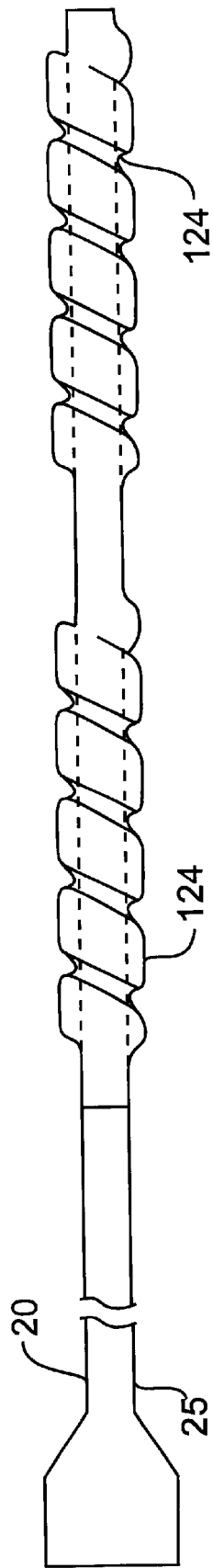
FIG. 11 is a schematic side elevational view of a portion of a central venous line catheter having two spiral balloons.

A preferred shape of the balloon is depicted in FIGS. 9–11 in accordance with the invention. As shown, e.g., in FIG. 9, the balloon 124 has a spiral shape. When the balloon 124 in the preferred embodiment is inflated, the balloon wraps in a spiral about the outer surface of shaft 25 of the catheter. The spiral has a major diameter (outer diameter) $d_1$ and a minor diameter (inner diameter) $d_2$. The minor diameter $d_2$ is only slightly larger than the diameter OD of the shaft 25. Although the number of turns in the spiral is not fixed, the preferred length of the balloon 124 is 50 to 80 mm, with a preferred distance of 7.5 to 18 mm between each turn of the spiral.

It is to be understood that the balloon 124 can extend the entire length of that portion of the central venous catheter that is intubated in the patient. Typically, this length is about 15–25 cm. Under these circumstances, the minor diameter $d_2$ of the balloon need not be larger than the outer diameter of a conventional central venous catheter, e.g., the minor diameter of the balloon can be 12 French, 10 French, or even as small as 7.5 French. More broadly, the balloon major diameter $d_1$, when the balloon extends along the entire length of the intubated portion of the catheter, can be 4–13 mm. In an arrangement where multiple balloons are used as described below, these balloons can cover the entire length of the intubated portion of the catheter. In one embodiment, two balloons, each having a length of about 50–80 cm can be used. Moreover, either two spiral balloons can be used, as shown in FIG. 11, or a spiral balloon and a straight balloon, as shown in FIG. 10. In another embodiment (not shown) three 50–80 cm long balloons can be used, either all spiral balloons, or a combination of spiral balloons and straight balloons.

As can be seen more clearly with reference to FIGS. 3 and 4, a pair of lumens 32 and 34 are formed in catheter 20, with lumen 32 serving as an inflow channel supplying balloon 24 with heat exchange fluid which is circulated through the catheter 20, while lumen 34 serves as an outflow channel returning the heat exchange fluid from the balloon 24 to the catheter. The particular heat exchange fluid selected is preferably biocompatible to avoid harm to the patient in the event of inadvertent rupture. The fluid is either cold or warm, depending on if patient cooling or patient heating is desired. Candidate materials include sterile saline water and carbon dioxide gas, although other fluids having suitable viscosity, heat exchange and material compatibility characteristics can also be used. While less desired because it is not biocompatible, freon can alternatively be used.

Balloon 24 is in fluid communication with lumens 32 and 34 via a plurality of ports such as inlet port 26 and outlet port 28. Heat exchange fluid circulated in catheter 20 passes from lumen 32 into balloon 24 through inlet port 26, then out of balloon 24 to lumen 34 through outlet port 28. While in the balloon 24, the heat exchange fluid, which is remotely cooled (or heated) outside the central venous line catheter 20, serves to provide a cold temperature fluid (or warm temperature fluid) flowing past the inner surface of the sheet material 38 which forms the walls of balloon 24. With a body fluid, such as blood, flowing exteriorly of the balloon 24, heat transfer occurs across the sheet material 38, effectively cooling (or heating) the body of the patient. To that end, inlet port 26 is positioned distally of outlet port 28.

Heat exchange fluid entering spiral balloon 124 will attempt to separate into parallel laminar layers, as in the known cooling catheters. However, because of the turns in the spiral, and because the minor diameter $d_2$ of the spiral balloon 124 is only slightly larger than diameter OD of the shaft 25, almost none of the fluid can take the short path, i.e., the path along the axis of the balloon 124. Instead, the fluid in the different layers will mix together in the longer path, adjacent the outer wall of sheet material 38 of the spiral balloon, wherein the path length substantially equals the circumference of the balloon 124 divided by the cosine of the spiral angle, multiplied by the number of turns in the spiral. This spiral path causes a high rate of fluid mixing. This mixing of the fluid layers places more of the cooling fluid adjacent wall 38 of balloon 124, hence, more of the fluid is available to exchange heat with the blood outside the balloon. In addition, the longer path results in longer residence time for the heat exchange fluid in the balloon. Both of these results significantly increase the cooling capacity of the catheter.

The expandable straight balloon 24 and expandable spiral balloon 124 can be collapsed for insertion of the catheter into the patient's body, and inflated after insertion into the vein, so that the size of the incision in the patient's body need only be slightly larger than the OD of the catheter shaft 25.

In addition, it is believed that blood in the vein flowing past the spiral-shaped balloon 124 will mix together more effectively, and will not remain in separate laminar layers, because of the turns in the spiral of balloon 124, again promoting more efficient heat transfer by exposing more blood to the heat transfer surface 38. In addition, as discussed above, since the balloon is expanded and has a smooth outer surface, blood flow past the balloon is smooth, and substantially avoids eddies and turbulence which could be caused when folds or wrinkles are present in a balloon outer surface. Such eddies and turbulence could cause stagnation and possible blood clotting.

Efficient heat transfer can also be promoted by specific considerations regarding the cross-sectional shape of the lumens 32 and 34. Specifically, as can be seen in FIG. 3, the lumens 32 and 34 are designed to maximize the volume of fluid flowing therethrough. This is accomplished by providing the lumens with crescent cross-sectional shapes which occupy circumferentially a maximum arc length in the catheter 20.

In order to facilitate fluid flow in and out of balloon 24, outlet port 28 can be made larger than inlet port 26 to reduce the resistance encountered by the heat exchange fluid as it exits the balloon 24. This relative size difference becomes particularly important when multiple balloons are provided in catheter 20, as is contemplated in accordance with an alternate embodiment of the invention. Specifically, although described above in terms of a single balloon 24, and 124, it will be appreciated that several such expandable heat exchange balloons can be provided, disposed axially along the length of shaft 25, as shown, for example, in FIGS. 10 and 11. One advantage of a multiple balloon configuration is that the flow and temperature of the heat exchange fluid can be more easily controlled along the entire length of the heat exchange region of the catheter 20. Realizing that the heat exchange fluid will be coolest prior to entering into heat exchange with the blood, and warmest after that heat exchange, one can advantageously control not only the velocity and volume of flow, but also the direction of flow within each of the balloons 24 or 124. Another advantage of a multiple balloon design is the ability of the catheter to bend and flex when placed in a curved vasculature. The multiple balloon design can include a single spiral balloon 124 preferably at the distal end, with one or more spiral balloons 124 at other locations, as shown in FIG. 11, or alternately, can include a combination of spiral balloons 124 and/or straight balloons 124 disposed along the length of the catheter, as shown in FIG. 10.

Catheter 20 can also be provided with two or three lumens 42, 44 and 46 in addition to lumens, 32 and 34. Lumens 42, 44 and 46 can serve a multiplicity of functions, including infusion of drugs such as chemotherapy, fluids and nutrition, access to syringes for sampling, and accommodation of various sensors, such as thermistors to monitor the patient, thus generally providing access to the central blood supply as dictated by the particular application. Additionally, central lumen 44 may be made of a different diameter than side lumens 42 and 46 in order to better support a guidewire for instance. The lumens may extend substantially the full length of catheter 20, from proximal end portion 27 to distal end portion 22. Alternatively, some of the lumens may extend only a partial length of the catheter. The number of lumens provided can be varied depending on the particular application.

Figure 7:
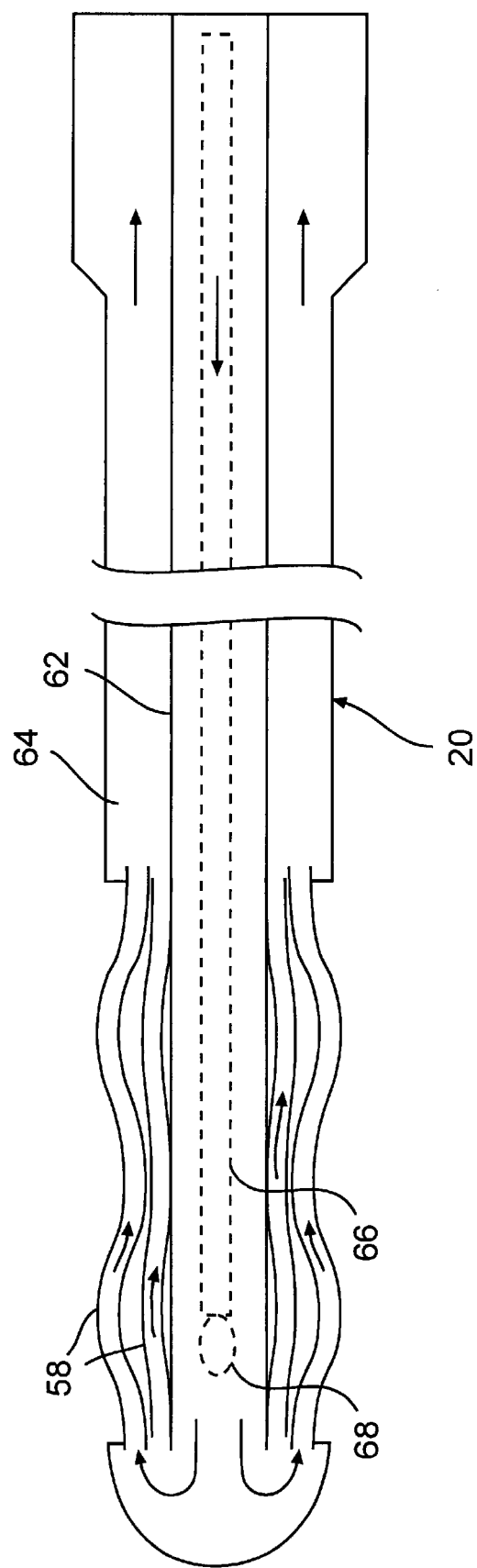
FIG. 7 is a schematic side elevational view of a central venous line catheter in accordance with a third embodiment of the invention.

It will also be appreciated that the heat exchange element does not necessarily need to be a balloon such as balloon 24 or 124. Rather, an arrangement such as a spiral array of flexible hollow fibers through which the heat exchange fluid is circulated can also be used, thus affording greater surface area for heat exchange interaction. A hollow fiber heat exchange element configuration is shown in FIG. 7. Hollow fibers 58 receive fluid from inner heat exchange fluid lumen 62 and return this fluid to outer heat exchange fluid lumen 64 of catheter 20. Additional lumens such as lumen 66 are also provided to facilitate delivery of fluids and for other uses. An important advantage of a hollow fiber heat exchange element arrangement is that it enables communication between the inner lumens, such as lumen 66, and the blood anywhere along the length of the heat exchange element, via for example port 68. With reference again to FIG. 1 and FIG. 2, the catheter 20 operates in conjunction with a temperature control module 50. A tubing set 52 (FIG. 1) including coolant inlet and outlet fittings 52a, 52b (FIG. 2) conveys fluid between temperature control module 50 and catheter 20 in a closed fluid circuit through which the fluid is circulated, using known pumping means (not shown) such as for example a diaphragm pump, bladder pump, piston pump, peristaltic pump, etc. It is to be understood that the inlet and outlet fittings 52a, 52b establish pathways of fluid communication from the temperature control unit 57 to the lumens 32, 34, respectively of the catheter 20. A temperature controller 55, which may be a microprocessor having appropriate information storage memory (not shown), is provided in temperature control module 50 and receives patient temperature signals from probe 54. By controlling the input to a temperature control unit 57, which may be a cooling device and/or a heating device in heat exchange relationship with the cooling fluid, temperature controller 55 automatically adjusts the temperature of the heat exchange fluid according to a desired target temperature or temperature range. The target temperature or range can be entered using an input device such as keyboard 56. A display device such as LCD 58 displays various parameters to provide indications of system operation and/or patient condition.

Preferably, the target temperature is selected to be normal body temperature, and any deviation from this temperature, for example induced by the onset of fever, is sensed by the probe 54 and automatically corrected by the system of the invention. Temperature correction is effected by for example activating temperature control unit 57 of temperature control module 50. In cooling applications, temperature control unit 57 causes cooling of the circulating fluid and ultimately the cooling of the patient's core body temperature, which is monitored by probe 54. When normal temperature is achieved, the temperature control unit 57 can then be automatically switched off or its cooling effect reduced by the temperature controller 55. Suitable temperature control algorithms taking into account performance parameters of system components and system time constants are implemented by temperature controller 55 to effect accurate temperature control. For more expedient temperature control, module 50 may also be provided with a heating device as part of the temperature control unit 57, which heating device can also be automatically activated, using feedback from probe 54, to for example prevent overshooting the desired target temperature or range, or even to induce hyperthermia in some situations. It will be appreciated that probe 54 can be used to provide temperature feedback from any part of the patient's body, rectally for instance, or it can provide temperature information anywhere in the fluid circuit, which information can then be correlated to the patient's core temperature using known parameters such as heat conductivity of different portions of the system and patient data such as weight, height, age, etc. Additionally, more than one probe can be used to provide combinations of readings from the patient and/or from the system to improve accuracy under some circumstances.

In accordance with the invention, the feedback scheme can be used to maintain desired temperature conditions for a patient. Specifically, the system can be used to control any temperature deviations from an acceptable temperature range, which may be a normothermic range, whereby probe 54 will trigger cooling or heating of the patient's body depending on this sensed deviation from the predetermined range. Moreover, since this deviation is generally indicative of certain physiological activity of which the patient's caretaker should be apprised, the operation of the system can be used as an indication that this physiological activity is taking place. For instance, when the cooling operation of temperature control unit 57 is activated due to a rise in the patient's core body temperature, the system cooling activity, as reflected in the increased workload of the cooling componentry of the system, is then used to indicate to the caretaker, audibly or visibly using an alarm or other status indicator device (not shown) for instance, that the patient's body is attempting to enter a fever state. Appropriate measures can then be taken, such as medical cultures to determine infection. Parameters other than workload can be used to provide this indication, such as the slope of the temperature feedback along with the sign of the slope. Alternatively, a direct indication of patient temperature as sensed by the probe 54 can be used. In this manner, use of the system for extended periods of time—for example, from about one hour to about twenty-nine or more days— is facilitated.

Referring to FIGS. 1 and 2, in addition to being connected to the temperature control unit 57, the central venous catheter 20 is connected to one or more central venous components 70, 72 (only two venous components shown in FIG. 1 for clarity of disclosure) via respective fittings 74, 76, 78 as appropriate (FIG. 2) to establish communication between the central venous components 70, 72 and selected lumens 42, 44, 46 of the catheter 20. As intended by the present invention, the central venous components 70, 72 can be established by one or more of: drug infusion sources, blood receptacles for receiving blood through the catheter 20, a guide wire, etc.

Additionally, as best seen in FIG, 2, the catheter 20 includes an anchor configured for affixing the catheter 20 to the patient. More specifically, in one intended embodiment, the anchor is established by a suture fitting 80. The suture fitting 80 can be made integrally with the catheter 20, or it can be made as a separate plastic fitting and surroundingly engaged with the catheter 20. As shown, the suture fitting 80 includes two eyes 82, 84 through which sutures can be positioned and engaged with the patient's skin or with a bandage or tape or other structure that has been fastened to the patient. Alternatively, the present anchor can be established by a piece of tape 86 that can tape the catheter of the present invention to the patient. Yet again, the present anchor can include another fastening device such as a plate with adhesive surface that can be engaged with the patient, with the plate including structure configured for receiving the catheter of the present invention. As understood herein, an anchor is desirable in a central venous catheter to hold the catheter on the patient, because a central venous catheter typically is intended for prolonged indwelling.

The above are exemplary modes of carrying out the invention and are not intended to be limiting. It will be apparent to one of ordinary skill in the art that modifications thereto can be made without inventive departure from the spirit and scope of the invention as set forth in the following claims.

We claim:

1. An intra-vascular catheter comprising:

a substantially elongate shaft having a length and a selected outer diameter O.D., and housing at least one lumen; and an expandable heat exchange having an exterior surface, a selected major diameter $d_1$ and a selected minor diameter $d_2$, and extending at least partially along the length of the shaft, the heat exchange element being shaped into at least one turn and having $d_2$ greater than O.D., to separate a heat exchange fluid flowing in said heat exchange element into laminar layers and to mix said laminar layers and boundary layers of heat exchange fluid flowing within said heat exchange element.

2. The catheter of claim 1 wherein the heat exchange element is configured in a spiral shape around the shaft.

3. The catheter of claim 1, further comprising a plurality of heat exchange elements.

4. The catheter of claim 3, wherein at least one of said plurality of heat exchange elements is configured in a spiral shape around the shaft.

5. The catheter of claim 1, further comprising anchor means for anchoring a portion of the shaft to a patient's body.

6. The catheter of claim 1, wherein the exterior surface of the heat exchange element, when the heat exchange element is expanded, is substantially wrinkle-free.

7. The catheter of claim 1, wherein the shape of the heat exchange element mixes boundary layers of fluid flowing outside the heat exchange element.

8. The catheter of claim 1, wherein the shape of the heat exchange element further promotes residence time of the heat exchange fluid in the heat exchange element.

9. An intravenous catheter comprising:

a substantially elongate shaft having a length and at least one lumen; and a heat exchange element extending at least partially along the length of the shaft, said heat exchange element having a spiral shape.

10. The catheter of claim 9, wherein said heat exchange element is expandable.

\* \* \* \* \*

UNITED STATES PATENT AND TRADEMARK OFFICE
CERTIFICATE OF CORRECTION

PATENT NO.    : 6,520,933 B1
DATED         : February 18, 2003
INVENTOR(S)   : Scott Evans et al.

It is certified that error appears in the above-identified patent and that said Letters Patent is hereby corrected as shown below:

Column 10,
Line 1, "exchange having" should read -- exchange element having --.

Signed and Sealed this

Twenty-second Day of July, 2003

JAMES E. ROGAN
*Director of the United States Patent and Trademark Office*